United States Patent [19]
Mitra et al.

[11] Patent Number: 5,318,999
[45] Date of Patent: Jun. 7, 1994

[54] DENTAL COMPOSITIONS PREPARED BY POLYMERIC PHOTOINIFERTER POLYMERIZATION OF THE DENTAL COMPOSITIONS AND SHAPED DENTAL ARTICLES PRODUCED THEREBY

[75] Inventors: Sumita B. Mitra, St. Paul; Mahfuza B. Ali, Woodbury, both of Minn.

[73] Assignee: Minnesota Mining and Manufacturing Company, St. Paul, Minn.

[21] Appl. No.: 772,116

[22] Filed: Oct. 8, 1991

Related U.S. Application Data

[63] Continuation of Ser. No. 454,176, Dec. 21, 1989, abandoned.

[51] Int. Cl.$^5$ .......................... C08F 2/48; C08F 4/00; C08F 293/00; A61K 6/08
[52] U.S. Cl. ..................... 522/57; 522/904; 522/908; 522/913; 522/182; 522/79; 522/81; 522/83; 523/115; 523/116; 523/117; 525/92; 525/94; 525/267; 525/299; 433/168.1; 433/228.1; 433/222.1
[58] Field of Search ............. 522/57, 908, 913, 182, 522/79, 81, 83; 523/117, 115, 116; 525/92, 94, 267, 299

[56] References Cited

U.S. PATENT DOCUMENTS

| | | | |
|---|---|---|---|
| 3,339,283 | 9/1967 | Van Handel | 32/2 |
| 3,391,231 | 7/1968 | Van Handel | 264/18 |
| 3,452,437 | 4/1969 | Chang | 32/15 |
| 3,819,568 | 6/1974 | Taylor et al. | 260/42.52 |
| 4,243,658 | 1/1981 | Chang | 424/52 |
| 4,300,886 | 11/1981 | Süling et al. | 433/202 |
| 4,360,344 | 11/1982 | Colpitts | 433/199 |
| 4,428,930 | 1/1984 | Chang | 424/52 |
| 4,432,730 | 2/1984 | Gettleman et al. | 433/168 |
| 4,490,115 | 12/1984 | Orlowski et al. | 523/117 |
| 4,503,169 | 3/1985 | Randklev | 523/117 |
| 4,510,127 | 4/1985 | Chang | 424/52 |
| 4,579,881 | 4/1986 | Masuhara et al. | 523/120 |
| 4,661,065 | 4/1987 | Gettleman et al. | 433/168.1 |

FOREIGN PATENT DOCUMENTS

| | | | |
|---|---|---|---|
| 0286376 | 6/1988 | European Pat. Off. | C08F 220/00 |
| 0349-232 | 6/1989 | European Pat. Off. | C08F 293/00 |
| 0349270 | 6/1989 | European Pat. Off. | C09J 153/00 |
| 63-278910 | 11/1988 | Japan | C08F 2/50 |
| 63-308055 | 12/1988 | Japan | C08L 27/12 |
| 64-24879 | 1/1989 | Japan . | |
| 64-29410 | 1/1989 | Japan . | |
| 3-9914 | 1/1991 | Japan | C08F 293/00 |
| 1278413 | 4/1968 | United Kingdom . | |

OTHER PUBLICATIONS

Die Makromolekulare Chemie Rapid Communications, vol. 3, No. 1, 1982, Huthig & Wepf Verlag, T. Otsu et al. "Role of Initiator-Transfer Agent-Terminator (Iniferter) in Radical Polymerizations: Polymer Design by Organic Disulfides as Iniferters", pp. 127–132.

(List continued on next page.)

*Primary Examiner*—Susan Berman
*Attorney, Agent, or Firm*—Gary L. Griswold; Walter N. Kirn; Janice L. Dowdall

[57] ABSTRACT

The present invention provides a novel dental composition and a method of making shaped dental articles therefrom via photoiniferter polymerization. The dental composition comprises acrylic photoiniferter block polymer, a monomer charge comprising free radically polymerizable acrylic monomer, and a filler and optionally includes pigments, sensitizers, medicaments, stabilizers, accelerators, etc. The dental composition is alternately exposed to a source of radiant energy and shaped in a desired manner in order to form a partially cured dental article. The partially cured dental article is then cured by a final exposure to the radiant energy source, providing a final cured article. The resultant reinforced acrylic copolymer system provides a shaped dental article which can be a denture base, a denture liner or a restorative.

24 Claims, No Drawings

OTHER PUBLICATIONS

Polymer Bulletin, vol. 7, No. 1, 1982, Springer-Verlag, T. Otsu et al. "Efficient Synthesis of Two or Multi Component Block Copolymers Through Living Radical Polymerization with Polymeric Photoiniferters", pp. 197–203.

Restorative Dental Materials, Seventh Edition (R. C. Craig ed.), C. V. Mosby Company (1985) pp. 225–252, 458–511.

E. A. Lewis, R. E. Ogle, and S. E. Sorensen, Orthodonic Application of a New Visible Light Curing Resin System, NYS Dental Journal, Mar. 1986, pp. 32–34.

Clinical Research Associates Newsletter, vol. 10(1), Jan. 1986.

Otsu et al., *Living Radical Polymerizations in Homogeneous Solution by Using Organic Sulfides as Photoiniferters*, Polymer Bulletin, (1982) pp. 45–50.

Otsu et al., *Living Mono– and Biradical Polymerizations in Homogeneous System Synthesis of AB and ABA Type Block Copolymers*, Polymer Bulletin, 11 (1984) pp. 135–142.

Lewis et al., Orthodonic Application of a New Visible Light Curing (VLC) Resin System, NYS Dental Journal, Mar. 1986, pp. 32–34.

M. Braden, Tissue Conditioners: I. Composition and Structure, Dental School of the London Hospital Medical College, University of London, London, England.

Triad® Dental System, Dentsply/York Division, Dentsply International Inc. York, Pa.

J. P. Trivedi and I. D. Shah, Indian J. Pharm., 25, 421 (1963).

D. Kessel and R. S. McElhinney, Mol. Pharmacol., 14(6), 1121–9.

DENTAL COMPOSITIONS PREPARED BY POLYMERIC PHOTOINIFERTER POLYMERIZATION OF THE DENTAL COMPOSITIONS AND SHAPED DENTAL ARTICLES PRODUCED THEREBY

This is a continuation of application Ser. No. 07/454,176 filed Dec. 21, 1989 now abandoned.

TECHNICAL FIELD

The invention relates to dental compositions which can be used to make shaped dental articles, including prostheses, such as denture bases and denture liners, and restoratives by the controlled and gradual curing of the dental compositions via photoiniferter polymerization, the method of making the shaped dental articles via photoiniferter polymerization, and the shaped dental articles produced by the method.

BACKGROUND OF THE INVENTION

Dentures are conventionally made from plastic materials. The tooth-holding portion of a denture is generally made from a rigid polymeric material of good dimensional stability and high impact strength. The gum portion frequently causes discomfort to the denture wearer. Consequently, much of the denture art has been concerned with providing comfort as well as a good fit to the denture wearer. Attempts have been made to alleviate denture wearer discomfort by providing denture liners made of soft elastomeric materials.

The most commonly used type of polymeric material from which denture bases and denture liners have been made is acrylic plastic. Many different types of acrylate polymers, copolymers, and crosslinked systems have been utilized for denture bases and denture liners. A detailed review of such materials is presented in *Restorative Dental Materials*, Seventh Edition (R. C. Craig ed.), C. V. Mosby Company, (1985), pp. 458–511. In general, the method of fabrication of such materials involves the free radical polymerization of acrylate monomers.

Most denture base plastics are prepared from powder-liquid compositions comprising poly(methyl methacrylate) beads, free radical polymerization initiator such as benzoyl peroxide, and monomer liquid consisting primarily of methyl methacrylate. Polymer beads comprising higher alkyl methacrylates, such as poly(ethyl methacrylate) and poly(butyl methacrylate), are typically used in the preparation of denture liners in order to provide flexibility to the denture liner. Lower acrylate beads are typically used in the preparation of denture bases. A method of making dental articles such as denture bases and denture liners involves mixing the appropriate polymerized beads and liquid monomer in order to form a mixture, packing the mixture in prepared flasks, followed by curing the mixture by the application of heat and pressure. Cold-curing systems which utilize amine accelerators are available, but, in general, provide acrylic polymers having inferior properties. Both the heat-curing process as well as the cold-curing process are labor intensive and require lengthy time periods of several hours.

In the dental fields of denture bases and denture liners, modifications to basic polymer systems have been made in an attempt to enhance the physical properties of the denture bases and the denture liners in order to provide both a good fit and comfort to the denture wearer. However, modifications to denture base materials and denture liner materials to meet these criteria have not met with complete success.

For example, U.S. Pat. No. 4,300,886 describes a denture base made of a rigid polymethacrylate elasticized by means of diamine lengthened polyurethane. However, such a modification compromises the physical properties of the denture base.

When both unmodified and modified denture base materials failed to provide the comfort sought after by the denture wearer, denture liners were fabricated to make the denture bases more comfortable. A variety of soft elastomeric materials were formulated for use in either combination with the denture base or in integral formation with the denture base, such as those compositions disclosed in U.S. Pat. Nos. 3,339,283; 3,391,231; and 4,360,344. U.S. Pat. Nos. 3,391,231 and 3,339,283 describe a method of fabricating an artificial denture by first molding a rigid denture base and then covering it with a hydraulic cushioning means formed from a cold cure silicone rubber.

U.S. Pat. No. 4,360,344 describes a composite denture, wherein the tooth-holding portion is fabricated from a hard acrylic polymer and the mouth-engaging portion is fabricated from a soft non-hydrophilic polyurethane elastomer.

Each of the above polymers are prepared according to conventional free-radical polymerization processes. Thus, the processes once started and stopped provide materials of certain physical properties and shape which cannot be further modified without the inclusion of additional initiator. Thus, the above-described polymerization processes do not possess a "living" character.

The shaped dental articles prepared by the above-described methods are oftentimes uncomfortable for the dental patient and provide a poor fit. Dental articles also are difficult to fabricate utilizing the above-described methods.

A need therefore exists for denture bases and denture liners which are both comfortable and which provide a good fit to the denture wearer. In addition, a need exists for denture bases and denture liners which are easy to fabricate. A need also exists for denture bases and denture liners which can be gradually cured by allowing the dental practitioner to start and stop the curing process at will.

Also used in dentistry, are restoratives based upon polymerizable diacrylates or dimethacrylates containing conventional free radical initiators. Such restoratives are discussed in the aforementioned reference entitled *Restorative Dental Materials*, pp. 225–252. The term "extraoral restorative" as used herein refers to a restorative made and cured outside the mouth which is subsequently placed inside the mouth. The term "direct restorative" as used herein refers to a restorative placed and cured directly in the mouth such as a tooth-colored composite restorative resin useful as a tooth-filling material.

The curing of known compositions used in forming restoratives occurs via a free radical chain reaction. Once terminated, the polymerization cannot be reinitiated simply by further light exposure and hence the customary practice is for the dental practitioner to first cure the restorative fully, and then use a dental tool, such as a bur, to cut back and shape the cured restorative to the desired anatomy. This is a time-consuming process for the dental practitioner and uncomfortable for the patient if the occlusion obtained is not correct.

The concept of light curing or cure on demand is currently gaining popularity in the field of dentistry. Recently a light activated denture base resin has been marketed under the tradename Triad$^R$ by Dentsply Corporation. The materials of this system consist of a prepolymerized polymethylmethacrylate embedded in a crosslinked network of a urethane dimethacrylate. These materials are discussed in an article by E. A. Lewis, R. E. Ogle, and S. E. Sorensen, *Orthodontic Applications of a New Visible Light Curing Resin System*, NYS Dental Journal, March, 1986, p. 32-34. Acrylate polymerizations, both chemical and light activated, are also used extensively in direct esthetic restoratives.

The aforementioned light activated systems represent classical free radical polymerizations. The molecular weight increases rapidly with time so that the extent of polymerization and crosslinking cannot be controlled by light exposure. Although the light curing aspect is an attractive feature of these systems, the properties of these materials are not as good as the heat cured materials. According to Clinical Research Associates (CRA) the best application of these materials appears to be for chair-side repairs and relining. (CRA Newsletter, Vol. 10(1), January 1986).

In all applications thus far in dentistry, the polymerization mechanism utilized has involved simple free radical kinetics. Thus, the molecular weight reaches its peak value very early during the polymerization and although extended time of reaction leads to greater conversion, this is not attendent with increased molecular weight. During the light activated polymerizations of dental materials known thus far, once the polymerization has been stopped by turning off the light source, it cannot be reinitiated by turning the light source back on.

A need therefore exists for direct and indirect restoratives, in addition to denture bases and denture liners, which can be cured gradually by allowing the dental practitioner to start and stop the curing process at will. Applicants have discovered a composition which employs iniferter technology.

The term "iniferter" or "photoiniferter" refers to a chemical compound that has a combined function of being a free radical <u>ini</u>tiator, trans<u>fer</u> agent, and <u>termina</u>tor, the term "iniferter" being a word formed by the underlined portions of the terms identifying these functions. The photo portion of the term indicates that the free radical polymerization is photolytically induced. This term and its use in the production of block copolymers is well known, particularly because of the work of Takayuki Otsu of the Department of Applied Chemistry, Osaka City University, Osaka, Japan. This work is discussed, for example, in an article by Otsu et al., entitled "Living Radical Polymerizations in Homogeneous Solution by Using organic Sulfides as Photoiniferters", Polymer Bulletin, 7, 45-50 (1982) and an article by Otsu et al., entitled "Living Mono- and Biradical Polymerizations in Homogeneous System Synthesis of AB and ABA Type Block Copolymers", Polymer Bulletin, 11, 135-142 (1984) and European Patent Application No. 88303088.7, Publication date Oct. 12, 1988, Publication Number 0,286,376. Despite the rather detailed description of making block copolymers according to such disclosures, there is no disclosure of dental compositions comprising acrylic photoiniferter block polymers and free radically polymerizable monomer which are suitable for the gradual and controlled formation of dental articles such as denture bases, denture liners, and restoratives.

Copending U.S. application Ser. No. 08/024,798, filed Mar. 11, 1993, which is a continuation of U.S. application Ser. No. 07/596,575, filed Oct. 11, 1990, now abandoned, which is a continuation of U.S. application Ser. No. 07/356,650, filed May 19, 1989, now abandoned, which is a continuation-in-part of copending U.S. application Ser. No. 07/212,594, Ali et al., filed Jun. 28, 1988, (assigned to the assignee of the present case) discloses the use of iniferter technology in the preparation of acrylic block copolymers suitable for use in pressure-sensitive adhesive compositions.

Copending U.S. application Ser. No. 07/939,569, filed Sep. 3, 1992, which is a continuation of U.S. application Ser. No. 07/465,594, filed Jan. 18, 1990, now abandoned, which is a continuation of U.S. Ser. No. 07/212,593, filed June 26, 1988, now abandoned, Andrus Jr. et al., (also assigned to the assignee of the present case) discloses the use of iniferter technology in the preparation of acrylic block copolymers which can be tailored to provide optical clarity and resistance to oxidative and photochemical degradation.

The above references do not teach or suggest dental compositions comprising photoiniferter block polymer and free radically polymerizable monomer which can undergo stepwise polymerization to gradually increase the molecular weight and toughness of a dental article prepared therefrom upon controlled and intermittent exposure to ultraviolet or visible radiation by gradual polymerization and/or crosslinking.

BRIEF DESCRIPTION OF THE INVENTION

We have found a dental composition and a method of curing the dental composition in order to form shaped dental articles by a free-radical polymerization method which occurs in steps so that the extent of reaction, molecular weight, and cross-linking can be controlled simply by turning a light source on and off. Thus, the polymerization mechanism is a "living polymerization", i.e. it can be reinitiated simply by turning a previously extinguished light source back on. This provides great latitude in controlling the extent of polymerization so that a partially cured dental article can be formed from the dental composition and shaped to a desired form or anatomy before final cure.

The dental composition of the present invention comprises reinforced acrylic photoiniferter block polymer, a monomer charge comprising free radically polymerizable monomer, and a filler. The reinforced acrylic photoiniferter block polymer possesses phase separated domains, thus offering flexibility along with toughness to dental articles formed from the dental composition. A photoiniferter is used as a means of promoting, controlling, and terminating polymerization of the photoiniferter block polymer. The photoiniferter block polymer is in turn used as a means of controlling and terminating polymerization of polymers of more advanced architecture useful as shaped dental articles by adding free radically polymerizable monomer to the photoiniferter block polymer in addition to a filler in order to form a dental composition.

The photoiniferter block polymer contained in the dental composition can undergo further polymerization by chain extension and/or crosslinking with the free radically polymerizable monomer with which it is combined in order to form a partially cured dental article. This is followed by the alternating steps of curing by intermittent exposure to actinic radiation (i.e., ultraviolet or visible radiation having a wavelength of about 200 nm to about 800 nm) and shaping of the article in order to form a final cured shaped dental article. This is accomplished without the use of additional polymerization initiators such as light activated initiators. The control of the polymerization in preparing the photoiniferter block polymer provided by the iniferter technology and the control of the polymerization and/or crosslinking in preparing the shaped dental articles from the dental composition comprising photoiniferter block polymer, free radically polymerizable monomer, and filler, permits the preparation of denture bases, denture liners and restorative compositions having controllable properties. By controlling the extent of cure, the physical nature of the material, i.e. its carvability, moldability, etc., as well as its mechanical strength and toughness can be controlled. The generation of toughened thermosets by this technology provides shaped dental articles such as denture bases, denture liners, and restoratives of improved physical properties such as ultimate strength, fracture toughness, and wear over existing materials.

The terms "thermoset" and "thermosetting" as used herein refer to high polymers that solidify or "set" irreversibly when heated. This property is usually associated with a crosslinking reaction of the molecular constituents induced by heat or radiation.

The term "acrylic photoiniferter block polymer" as used herein refers to a homopolymer or block copolymer segment prepared by the photoiniferter polymerization of acrylic monomer which is useful in the dental composition of the present invention. The acrylic photoiniferter block polymer is capable of polymerizing free radically polymerizable monomer with which it is combined upon being subjected to a radiant energy source in order to form a shaped dental article.

A first aspect of the present invention relates to a dental composition comprising:

(a) a mixture of
(i) an acrylic photoiniferter block polymer selected from the group consisting of $I(BT)_n$, $I(BAT)_n$, and mixtures thereof, wherein I represents the free radical initiator portion of an iniferter of the formula $I(T)_n$;

T represents the terminator portion of the iniferter;

n is an integer of at least 1;

B represents an acrylic polymer block of suitable molecular weight;

A represents a normally thermoplastic polymer block having a glass transition temperature of at least about 30° C.;

(ii) a monomer charge comprising free radically polymerizable monomer of the formula $C(D)_x$ wherein x is an integer ranging from 1 to about 9;

D is an ethylenically unsaturated monovalent moiety; and

C is an organic residue; and (iii) about 5 to about 90 weight % of a filler based upon the weight of said mixture;

wherein the weight ratio of the acrylic photoiniferter block polymer to the free radically polymerizable monomer of the formula $C(D)_x$ ranges from about 1:99 to about 99:1, and wherein controlled and intermittent exposure of the mixture to a radiant energy source capable of emitting radiation in a range of from about 200 to about 800 nm results in the partial polymerization or crosslinking of the acrylic photoiniferter block polymer and free radically polymerizable monomer to form a partially cured dental article capable of being shaped, after which a final exposure to the energy source provides a final cured dental article.

A second aspect of the present invention relates to a method of making a dental article comprising the steps of:

(i) forming a mixture of (a) acrylic photoiniferter block polymer selected from the group consisting of $I(BT)_n$, $I(BAT)_n$, and mixtures thereof, wherein I represents the free radical initiator portion of an iniferter of the formula $I(T)_n$;

T represents the terminator portion of said iniferter;

n is an integer of at least 1;

B represents an acrylic polymer block of suitable molecular weight; and

A represents a normally thermoplastic polymer block having a glass transition temperature of at least about 30° C.;

(b) a monomer charge comprising free radically polymerizable monomer of the formula $C(D)_x$ wherein x in an integer ranging from 1 to about 9;

D is an ethylenically unsaturated group; and

C is an organic residue; and (c) about 5 to about 90 weight % of a filler based upon the weight of said mixture;

wherein the weight ratio of the acrylic photoiniferter block polymer to free radically polymerizable monomer of the formula $C(D)_x$ ranges from about 1:99 to about 99:1;

(ii) exposing the mixture to radiation of about 200 to about 800 nm from a radiant energy source until polymerization or crosslinking of the acrylic photoiniferter block polymer and free radically polymerizable monomer occurs in order to form a partially cured dental article;

(iii) shaping the partially cured dental article of step (ii) as desired;

(iv) repeating steps (ii) and (iii) if necessary until the desired shape of the partially cured dental article has been obtained; and (v) exposing the partially cured dental article of either step (iii) or step (iv) to a final exposure of radiation in order to form a final cured dental article.

A third aspect of the invention relates to shaped dental articles formed according to the method of the invention. The term "shaped dental article" as used herein refers to prostheses such as denture bases and denture liners, direct restoratives, and extraoral restoratives.

The shaped dental articles comprise as part of their polymer matrix cured reinforcing acrylic block copolymers. The use of "living" photoiniferter polymerization permits the interruption of the polymerization and/or crosslinking of the photoiniferter block polymer and $C(D)_x$ monomer at any time at which an intermediate or final desired physical consistency of the dental article has been attained. This enables polymerization of an initially fluid dental composition to intermediate putty stages at which it can be shaped, molded, cast, or carved to desired specifications and then finally cured to a hard set upon further exposure to radiation. For example, a dental practitioner may wish to terminate the curing process for a period of time in order to check the dental article such as a denture base, a denture liner or an extraoral restorative such as a tooth filling for proper fit. In the case of a direct restorative (i.e., a restorative placed and cured directly in the mouth), the dental practitioner may wish to terminate the curing process for a period of time in order to check the bite and carve in the required anatomy. By additional exposure to a radiant energy source the polymerization process may then be continued to provide the final shape to the dental article.

Thus, the use of the dental composition and method of the present invention results in a very substantial time savings for the dental practitioner and greatly increases the ease with which shaped dental articles can be fabricated. Additionally, the use of the shaped dental articles of the present invention results in a dramatic increase in comfort and a superior fit for the dental patient.

DETAILED DESCRIPTION OF THE INVENTION

I. Dental Composition of the Present Invention and Preparation Thereof

The dental composition of the invention comprises acrylic photoiniferter block polymer combined with a monomer charge comprising free radically polymerizable monomer of the formula $C(D)_x$ and a suitable filler.

I.A. Photoiniferter Block Polymer

The first step in preparing the dental composition of the present invention involves the preparation of photoiniferter block polymer by using a photoiniferter compound in order to free radically polymerize one or two free radically polymerizable monomer charges in order to form photoiniferter block polymer of the formula $I(BT)_n$ or $I(BAT)_n$, respectively. The photoiniferter block polymer can be prepared according to the method of co-pending U.S. Pat. application Ser. No. 07/212,593, filed Jun. 26, 1988, Andrus, Jr. et al., incorporated by reference herein.

A monomer charge comprising free radically polymerizable acrylic monomer is dissolved in a suitable inert solvent, if needed, and polymerized by a first free radical polymerization utilizing a suitable iniferter of the formula $I(T)_n$ as a free radical initiator source in order to form a photoiniferter block polymer of the formula $I(BT)_n$. Generally, from about 0.01 to about 5 percent by weight of iniferter based upon the total weight of polymerizable composition is used.

The iniferter is caused to dissociate to form free radicals $I(\cdot)_n$ and $nT\cdot$ by exposure to an appropriate energy source. The preferred iniferter is one which will dissociate upon exposure to a radiant energy source, such as an ultraviolet or visible light source, preferably an ultraviolet radiant energy source. Upon exposure to the energy source, the iniferter dissociates to form free radicals which promote free radical polymerization of acrylic monomer of the first monomer charge. Upon completion of the free radical polymerization of the free radically polymerizable acrylic monomer to form free radical polymer segment $I(B\cdot)_n$ the energy source is discontinued to permit the free radically polymerized segment $I(B\cdot)_n$ to recombine with the terminator portion $nT\cdot$ of the iniferter to form photoiniferter block polymer of the formula $I(BT)_n$.

In order to prepare the photoiniferter block copolymer of formula $I(BAT)_n$, a second monomer charge comprising free radically polymerizable acrylic monomer is combined with the photoinferter block polymer $I(BT)_n$ in order to form a second mixture. The second mixture is exposed to the energy source in order to cause dissociation of $I(BT)_n$ to form free radicals $I(B\cdot)_n$ and $nT\cdot$ and the free radical polymerization of the second monomer charge onto the first polymer segment $I(B\cdot)_n$, that now being the initiator of the second free radical polymerization. Upon completion of polymerization of the second monomer charge, exposure to the energy source is terminated and the terminator portion $nT\cdot$ of the iniferter combines with $I(BA\cdot)_n$ to form photoiniferter block polymer of the formula $I(BAT)_n$.

The particular energy source and its intensity are selected to result in the dissociation of the photoiniferter to form free radicals. When employing a photoiniferter which will dissociate upon exposure to ultraviolet light radiation, an ultraviolet light source is utilized. When employing a photoiniferter which will dissociate upon exposure to visible light radiation, a visible light source is utilized. The intensity or rate of radiation is chosen such that it will advance the polymerization at a reasonable rate without deleteriously affecting the polymer segment being produced. A light source having a wavelength on the order of 200 to 800 nm, preferably about 300 to 400 nm, spaced approximately 10 cm from the reaction vessel, to provide an exposure of 2 milliwatts per square centimeter has been found to produce suitable results.

Reaction times on the order of 2 to 50 hours in the absence of a metal compound accelerator have been found to be typical, depending upon the intensity of the radiation, with faster reaction times being observed at greater intensities. Reaction times in the presence of a metal compound accelerator such as those disclosed in copending concurrently filed application Serial No. 07/454,374, now U.S. Pat. No. 5,093,385, Ali, A Method of Accelerating Photoiniferter Polymerization, Polymer Produced Thereby and Product Produced Therewith, incorporated by reference herein, have been found to be about 0.2 to about 5 hours.

The reactions involving the preparation of the photoiniferter block polymers $I(BT)_n$ and $I(BAT)_n$ are preferably conducted in a vessel with agitation to permit uniform exposure of the reactants to the energy source. While most of the reactions involving the preparation of photoiniferter block polymers have been conducted by employing a batch process, it is possible to utilize the same technology in a continuous polymerization operation.

Photoiniferter block polymer selected from the group consisting of $I(BT)_n$, $I(BAT)_n$, and mixtures thereof, the preparation of which is described above, is subsequently mixed with a monomer charge comprising free radically polymerizable monomer of the formula $C(D)_x$ in order to provide the dental composition of the present invention which can be cured in stages in order to provide a shaped dental article.

I.A.(i) Photoiniferters

Photoiniferters useful in forming the photoiniferter block polymer useful in the dental compositions of the present invention are those of the general formula $I(T)_n$, wherein $I\cdot$ represents the free radical initiator portion of an iniferter of the formula $I(T)_n$, $T\cdot$ represents the terminator portion of said iniferter, and $n$ is an integer of at least 1.

The preferred photoiniferters for use in producing the photoiniferter block polymers useful in the dental compositions of the invention are those represented by the formulae:

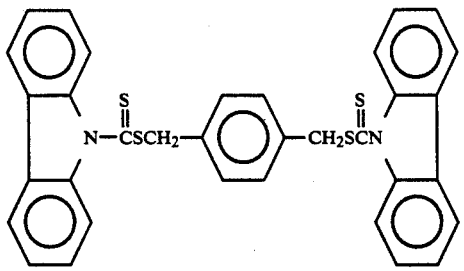

xylylene carbazoyldithiocarbamate [XCDC];

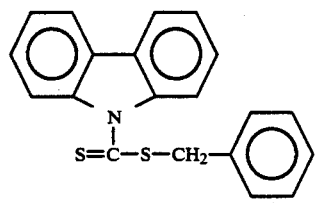

benzyl carbazolylthiocarbamate [CDC]
(monofunctional photoiniferter);

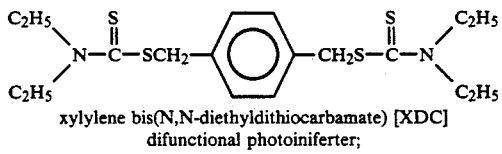

xylylene bis(N,N-diethyldithiocarbamate) [XDC]
difunctional photoiniferter;

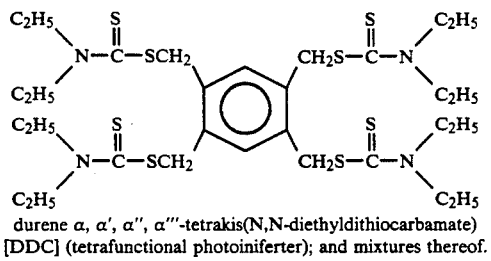

durene α, α', α", α'"-tetrakis(N,N-diethyldithiocarbamate)
[DDC] (tetrafunctional photoiniferter); and mixtures thereof.

I.A.(ii) Polymer Block B

Polymer block B of the photoiniferter block polymer of the formula $I(BT)_n$ or $I(BAT)_n$, comprises an acrylic polymer block of suitable molecular weight. Polymer block B should have a suitable molecular weight such that the shaped dental article formed from the dental composition possesses the desired mechanical properties. Typically, the molecular weight of the polymer block B for $I(BT)_n$ or $I(BAT)_n$ ranges from about 1000 to about 50,000. Preferably, the monomer used in forming polymer block B is monofunctional in order to avoid crosslinking. Monomers useful in forming polymer block B include but are not limited to those selected from the group consisting of acrylic acid; methacrylic acid; esters of acrylic acid and alcohol wherein the alcohol comprises from 1 to about 22 carbon atoms; esters of methacrylic acid and alcohol wherein the alcohol comprises from 1 to about 22 carbon atoms; and mixtures thereof. Examples of such esters include methyl methacrylate, isobornyl methacrylate, phenethyl methacrylate, isopropyl methacrylate, n-propyl methacrylate, n-butyl acrylate, ethyl acrylate, 2-ethylhexyl acrylate, isobutyl acrylate, methyl acrylate, n-propyl acrylate, iso-octyl acrylate, and the like. Optionally, one or more non-interfering oxygen, nitrogen, sulfur, fluorine, and phosphorous containing functionalities can be present on the monomers useful in forming polymer block B.

The preferred monomers for use in forming polymer block B include methyl methacrylate, isobornyl methacrylate, phenethyl methacrylate, n-butyl acrylate, ethyl acrylate, iso-octyl acrylate, and mixtures thereof. Optionally, one or more non-interfering oxygen, nitrogen, sulfur, fluorine, and phosphorus containing functionalities can be present on such monomers.

For photoiniferter block polymers of the formula $I(BT)_n$ polymer block B preferably has a glass transition temperature ranging from about $-200°$ C. to about $400°$ C. For photoiniferter block polymers of the formula $I(BAT)_n$ polymer block B preferably has a glass transition temperature ranging from about $-200°$ C. to about $100°$ C. In addition, the glass transition temperature of polymer block B is preferably at least about $500°$ C. lower than the glass transition temperature of polymer block A for $I(BAT)_n$ in order to obtain shaped dental articles having a range of properties.

I.A.(iii) Polymer Block A

Polymer block A of the photoiniferter block polymer $I(BAT)_n$ comprises a normally thermoplastic polymer block having a glass transition temperature $(T_g)$ of at least about $30°$ C. Preferably, the monomer used in forming polymer block A is monofunctional in order to avoid crosslinking. Preferably, the $T_g$ of polymer block A is about $50°$ C. higher than the $T_g$ of polymer block B for the photoiniferter block polymer $I(BAT)_n$. Preferably, polymer block A has a glass transition temperature ranging from about $30°$ C. to about $150°$ C. and polymer block B has a glass transition temperature ranging from about $-200°$ C. to about $100°$ C. for photoiniferter block polymer $I(BAT)_n$.

Monomers useful in forming polymer block A include but are not limited to methyl methacrylate, phenethyl methacrylate, isobornyl methacrylate, isopropyl methacrylate, n-propyl methacrylate, and mixtures thereof. The preferred monomers for use in forming polymer block A are selected from the group consisting of methyl methacrylate, isobornyl methacrylate, phenethyl methacrylate, and mixtures thereof.

I.A.(iv) Preferred Photoiniferter Block Polymers

The preferred photoiniferter block polymers for use in the dental composition of the present invention are those wherein n is an integer ranging from 1 to about 12 for $I(BT)_n$ and from about 2 to about 12 for $I(BAT)_n$. Most preferably, n ranges from 1 to about 6 for $I(BT)_n$ and from about 2 to about 6 for $I(BAT)_n$.

For $I(BAT)_n$, the preferred weight ratio of polymer block B to polymer block A ranges from about 95:5 to about 5:95. Most preferably, the weight ratio of polymer block B to polymer block A ranges from about 20:80 to about 80:20 in order for phase separation and toughening to occur.

The preferred photoiniferter block polymers of the formula $I(BAT)_n$ for use according to the present invention are disclosed in copending U.S. application Ser. No. 07/212,593 incorporated by reference herein and include those which may be represented by the formula

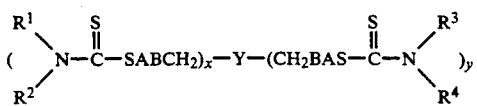

wherein $R^1$, $R^2$, $R^3$ and $R^4$ are aliphatic, aromatic, or substituted aromatic moieties, which can be the same or different and which do not substantially interfere with the ability of I· to promote free radical polymerization or with T· to recombine with I· or a polymer free radical segment including I·;

Y is a linking group having a functionality of $x+y$ which does not substantially interfere with the ability of I· to promote free radical polymerization or the ability of T· to recombine with I· or a polymer free radical segment including I·; and x and y are each integers of at least 1 and the sum of $x+y$ is not more than 12.

Preferably $R^1$, $R^2$, $R^3$, and $R^4$ which can independently be the same or different are selected from the group consisting of $C_{1-4}$ aliphatic moieties. An example of a suitable linking group Y is

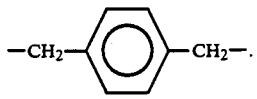

The selection of the photoiniferter block polymer for inclusion in the dental composition of the present invention depends upon the ultimate application of the dental composition. When a shaped dental article possessing greater flexibility and toughness is desired, the photoiniferter block polymer $I(BAT)_n$, wherein n is an integer greater than about 2, is preferably included in the dental composition.

$I(BT)_n$ and subsequently $I(BAT)_n$ can be made by a method having the following steps. An iniferter represented by the general formula $I(T)_n$ capable upon being subjected to an appropriate energy source of forming free radicals $I(\cdot)_n$ and $nT\cdot$ wherein I· is a highly reactive free radical capable of initiating free radical polymerization, and T· is a less reactive free radical which is generally much less capable of initiating free radical polymerization than I· but will rejoin with $I(\cdot)_n$ or a free radical polymer segment free radically polymerized with $I(\cdot)_n$ upon termination of said energy source is mixed with a first monomer charge consisting of acrylic monomer polymerizable to form an acrylic polymer block wherein the monomer is free radically polymerizable in the presence of $I(\cdot)_n$ to form a first polymer block. The mixture is exposed to an energy source capable of forming free radicals $I(\cdot)_n$ and $nT\cdot$. The exposure is maintained until the first monomer charge polymerizes with $I(\cdot)_n$ to form a free radical polymer segment represented by the formula $I(B\cdot)_n$ wherein B represents the first polymer block formed of the first monomer charge. Exposure is terminated whereby to cause $I(B\cdot)_n$ and $nT\cdot$ to combine to form a polymer represented by the formula $I(BT)_n$.

$I(BT)_n$ can be mixed with a second monomer charge which is free radically polymerizable in the presence of $I(B\cdot)_n$ to a second polymer block. $I(BT)_n$ is exposed to an energy source capable of forming free radical $I(B\cdot)_n$ and $nT\cdot$. The exposure is maintained until the second monomer charge polymerizes with $I(B\cdot)_n$ to form a free radical block copolymer segment represented by the formula $I(BA\cdot)_n$ wherein A represents the second polymer block formed of the second monomer charge. Exposure is terminated whereby $I(BA\cdot)_n$ and $nT\cdot$ combine to form a block copolymer represented by the formula $I(BAT\cdot)_n$.

Preferably, photoiniferter block polymer of the formula $I(BT)_n$ or $I(BAT)_n$ is used in the dental composition of the present invention rather than a combination of $I(BT)_n$ and $I(BAT)_n$ for practical considerations.

A person skilled in the area of dental products will recognize that by the judicious selection of dental composition components one can prepare dental compositions useful in forming dental bases, denture liners, and dental restoratives such as direct restoratives and extraoral restoratives.

I.B. Free-Radically Polymerizable Monomer of the Formula $C(D)_x$

A monomer charge comprising free radically polymerizable monomer is combined with the photoiniferter block polymer in order to form the dental composition of the present invention. The free radically polymerizable monomer included in the dental composition has the general formula $C(D)_x$ wherein x is an integer of 1 to about 9;

D is an ethylenically unsaturated monovalent moiety; and

C is an organic residue.

D can comprise an ethylenically unsaturated monovalent moiety including but not limited to those of the following general formula

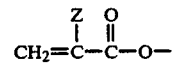

wherein

Z is selected from the group consisting of hydrogen, halogen, $C_{1-8}$ alkyl, and $C_{7-12}$ aryl alkyl. Preferably, D comprises the above structure wherein Z is selected from the group consisting of —H and —$CH_3$ for reasons of increased rate of polymerization. Most preferably, D comprises the above structure wherein Z comprises —$CH_3$ for reasons of reduced toxicity in addition to increased rate of polymerization.

C has been defined as an organic residue. Preferably the organic residue C comprises an alkyl group comprising from 1 to about 30 carbon atoms. Optionally, non-interfering oxygen, nitrogen, sulfur, phosphorus, and fluorine containing functionalities can be present in the alkyl residue. Useful organic residues are those that provide an optional balance of such factors as strength, durability, opacity or translucency, toxicity or irritancy, etc. For example, if a more rigid shaped dental article is desired C preferably comprises 1 to about 18 carbon atoms. More preferably, for a rigid shaped dental article, C comprises a hydrocarbyl residue comprising 1 to about 18 carbon atoms and 1 to about 10 noninterfering oxygen, sulfur or nitrogen atoms. Most preferably, for a rigid shaped dental article, C comprises 1 to about 18 carbon atoms and 1 to about 8 noninterfering oxygen, sulfur or nitrogen atoms.

Refractive indices of the dental compositions of the present invention should range from about 1.30 to about 1.70 prior to the addition of additives such as fillers or pigments, preferably from about 1.35 to about 1.65, and most preferably from about 1.40 to about 1.60.

Examples of suitable $C(D)_x$ monomers include but are not limited to alkyl, aryl, and aralkyl monoacrylates and monomethacrylates which optionally include one or more non-interfering heteroatoms (e.g., butyl acrylate, phenethyl methacrylate, norbornyl acrylate, isobornyl methacrylate, diglycidyl methacrylate); alkyl, aryl, and aralkyl diacrylates and dimethacrylates of diethylene glycol, triethylene glycol, 2,2-dimethylpropane diol, tetraethylene glycol, and hexane diol which optionally include one or more non-interfering heteroatoms (e.g. diethylene glycol diacrylate, diethylene glycol dimethacrylate, triethylene glycol diacrylate, triethylene glycol dimethacrylate, 2,2-dimethylpropane diol diacrylate, 2,2-dimethyl propane diol dimethacrylate, tetraethylene glycol diacrylate, tetraethylene glycol dimethacrylate, hexane diol diacrylate, hexane diol dimethacrylate, ethoxylated bisphenol A diacrylate, ethoxylated bisphenol A dimethacrylate [commonly known as BIS-GMA]); and alkyl, aryl, and aralkyl multifunctional acrylates and methacrylates which optionally include one or more non-interfering heteroatoms, (e.g., pentaerythritol trimethacrylates, pentaerythritol tetramethacrylates), and mixtures thereof.

The selection of free radically polymerizable $C(D)_x$ monomer can be made to facilitate the addition of fillers or additives, if needed or desired, to form the appropriate dental compositions of the invention. This is accomplished by selecting $C(D)_x$ monomer or a mixture of $C(D)_x$ monomer possessing a viscosity of about 10 to about 500 cps and a refractive index of about 1.30 to about 1.70. The preferred range of viscosity for mixtures of $C(D)_x$ monomer ranges from about 50 to about 360 cps. The preferred refractive index of $C(D)_x$ monomer ranges from about 1.40 to about 1.60.

It is possible to provide a dental composition which will provide a cross-linked network upon cure. If a diethylenically unsaturated $C(D)_x$ compound (wherein x equals 2) or a multi-ethylenically unsaturated $C(D)_x$ monomer compound (wherein x is greater than 2) is used a segmented cross-linked network is formed. This will provide increased fracture toughening properties to the resultant shaped dental articles. Preferably, x is greater than 2 in order to facilitate crosslinking.

The ratio of the photoiniferter block polymer to the free radically polymerizable monomer of the formula $C(D)_x$ in the dental composition of the invention can range from about 1:99 to about 99:1, preferably from about 10:90 to about 90:10, and most preferably from about 25:75 to about 75:25.

I.C. Fillers

Filler particles for use in the dental compositions of the present invention include organic fillers, inorganic fillers and mixtures thereof which are suitable for use in the oral environment and the like.

Examples of suitable inorganic fillers include but are not limited to diatomaceous or precipitated silica, powdered glass, powdered quartz, nitrides (e.g., silicon nitride), borosilicate glass, barium glass, hydroxyapatite, ceramic metal oxides (e.g., CaO, $Sb_2O_5$, $SnO_2$, $ZrO_2$, BaO, $Al_2O_3$ and $CACO_3$), submicron silica particles (e.g., pyrogenic silicas such as the Aerosil TM Series OX 50 TM, "130", "150" and "200" silicas sold by Degussa and Cab-O-Sil M5 TM silica sold by Cabot Corp.), and mixtures thereof.

Examples of suitable organic filler particles include but are not limited to filled or unfilled pulverized polyacrylates or polymethacrylates [e.g., poly(methyl methacrylate)], polycarbonates, polyepoxides, mixtures thereof and the like. Preferred filler particles comprise quartz, submicron silica, and non-vitreous microparticles of the type described in U.S. Pat. No. 4,503,169, which is incorporated by reference herein.

It is preferable to treat the surface of the filler particles with a coupling agent in order to enhance the bond between the filler and the organic polymer matrix. The use of such coupling agents is well known in the art. Examples of suitable coupling agents include gamma-methacryloxy-propyltrimethoxy silane, gamma-mercaptopropyltriethoxy silane, gamma-aminopropyltrimethoxy silane and the like.

Other types of useful fillers include inorganic-filled organic fillers such as those described in UK Patent No. 1,278,413, Publication Date Jun. 21, 1972. Useful filler particles can be either radiopaque or non-radiopaque depending upon the particular application. For dental compositions useful in forming denture bases and denture liners non-radiopaque fillers are acceptable. For dental compositions useful in forming restoratives, a radiopaque filler is preferred. About 5 to about 90 weight percent of a filler is included in the dental composition of the present invention, preferably about 40 to about 80 weight percent.

It is within the scope of this invention to include various other components in the dental composition formulations useful in forming denture base, denture liners, and dental restoratives. For example, it may be desirable to include such materials as colorants (e.g. pigments and/or dyes), stabilizers, sensitizers, metal compound accelerators, medicaments, and/or various polymeric additives. These materials are typically added to the dental composition prior to the exposure of the dental composition to the radiant energy source.

Metal Compound Accelerators

One or more metal compound accelerators may be added to the dental compositions of the invention according to copending concurrently filed U.S. application Ser. No. 07/454,374, Ali, A Method of Accelerating Photoiniferter Polymerization, Polymer Produced Thereby and Product Produced Therewith, incorporated by reference herein, to enhance the rate of polymerization of the photoiniferter block polymer and $C(D)_x$ monomer, thus speeding up the cure time. One or more metal compound accelerators may also be used in the initial preparation of the photoiniferter block polymer which is contained in the dental composition.

Thus, a polymerization accelerating amount of at least one metal compound which is capable of accelerating free radical polymerization may be added such that it is present during the polymerization of at least one monomer charge during the synthesis of the photoiniferter block polymer. In addition, a polymerization accelerating amount of at least one metal compound which is capable of accelerating free radical polymerization may be added to the dental composition of the present invention such that it is present during the preparation of the shaped dental article. The metal compound should not interact with the free radically polymerizable monomer to which it is added in order to form an insoluble compound in an amount which would substantially interfere with the polymerization or crosslinking reactions.

Preferably, the metal compound is represented by the general formula $M_xL_x$ wherein M is a cation having a valency of z of a metal which is selected from the group consisting of tin, zinc, cobalt, titanium, lead, and palladium;

x is an integer of at least 1;

L is an anion having a valency of x which is selected from the group consisting of

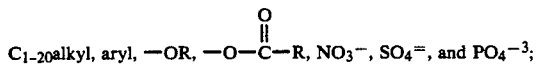

R is selected from the group consisting $C_{1-20}$ alkyl and aryl; and z is an integer of at least 1.

Most preferably, the metal compound is selected from the group consisting of stannous 2-ethylhexanoate, zinc 2-ethylhexanoate and mixtures thereof.

Preferably, about 0.1 to about 10 mole percent of metal compound is used based upon the monomer charge to which the metal compound added. Most preferably, about 1 to about 3 mole percent of metal compound is used based upon the monomer charge to which the metal compound is added. Such metal compound accelerator can be added to the dental composition mixture prior to the exposure of the dental composition mixture to the radiant energy source.

Photosensitizers

It may sometimes be advantageous to add to the dental composition an effective amount of a photosensitizer in order to obtain efficient transfer of radiation. Such photosensitizer can be added to the dental composition mixture prior to the exposure of the dental composition mixture to the radiant energy source. Examples of such photosensitizers are ketones, α-diketones,(α-β-unsaturated ketones coumarins, and the like. Preferably, the photosensitizer utilized comprises camphorquinone for reasons of greater depth of cure. About 0.05 to about 15 weight percent of a photosensitizer can be added to the dental composition, preferably about 0.1 to about 5 weight percent.

II. Method of Preparing of Shaped Dental Articles From the Dental Compositions of the Present Invention The method of preparing the shaped dental articles of the present invention begins with the preparation of the above-described dental compositions useful in forming the shaped dental articles. As indicated above, photoiniferter block polymer selected from the group consisting of $I(BT)_n$, $I(BAT)_n$, and mixtures thereof is mixed with free radically polymerizable monomer of the formula $C(D)_x$, a filler, and other additives such as sensitizers, etc. if needed or desired in order to form the dental composition of the present invention. The dental composition is then partially cured by exposure to a radiant energy source, followed by shaping. The partially cured dental article is then alternately shaped and cured by exposure to the radiant energy source until the desired cure is obtained. A mold may be used to contain and shape the dental composition while it undergoes curing. Depending upon the shaped dental article formed, the mold may preferably be transparent to radiation emitted from the radiant energy source. The radiant energy source utilized should emit ultraviolet or visible radiation in the range of about 200 to about 800 nm, preferably about 300 to about 800 nm for extraoral applications for health reasons. If the dental composition is cured in the mouth, visible radiation, from a visible light source such as a Visilux 2 ™ dental curing light (available from 3M) is preferably used.

As described earlier, the curing of the dental composition to form the shaped dental article is controlled by exposure to a radiant energy source capable of causing the desired extent of polymerization. Suitable radiation sources afford a combination of such properties as safety, controllability, intensity and distribution of incident energy. See generally, "Radiation Curing", Kirk-Othmer Encyclopedia of Chemical Technology, Third Edition, Vol. 19, p. 607–624 (1982). In general, any radiation source capable of emitting radiation of about 200 nm to about 800 nm can be used. Preferred radiant energy sources are ultraviolet or visible light sources.

EXAMPLES

The following detailed description includes exemplary preparations of photoiniferters, photoiniferter block polymers of the formula $I(BT)_n$, photoiniferter block polymers of the formula $I(BAT)_n$, and dental compositions produced therefrom which are useful in forming polymeric materials of the type useful as shaped dental articles. All parts and percentages are by weight unless otherwise specified.

Definitions of Terms

The number-average molecular weight ($\overline{M}_n$), and weight-average molecular weight ($\overline{M}_w$), are well known mathematical descriptions of the molecular weight distribution of a polymer sample.

The polydispersity, abbreviated "ρ", is a measure of the molecular weight distribution of a polymer and is defined as $\overline{M}_w/\overline{M}_n$.

Each of the foregoing is a well known term used by polymer chemists and others. Further explanation of the derivation of these terms may be found in Experimental Methods in Polymer Chemistry, Wiley and Sons, 1981, Chapter 3 entitled "Molecular Weight Averages", pages 57–61.

"Barcol Hardness" is a measurement of hardness. Barcol Hardness measurements were taken of the dental compositions of the present invention at various stages of cure. The Barcol Hardness measurements were taken using a Barcol Hardness Indenter Tester available commercially from the Barber Colman Company, yielding hardness values of the "B" scale. For the following Examples when the Barcol hardness measurement was low (e.g. 0–20) curing was not yet complete and the dental composition material was still carvable. When the Barcol hardness measuement was high (e.g. 30–50) the dental composition material was glassy and nearly fully cured.

EXAMPLES 1–3

Examples 1, 2 and 3 describe the preparation of a monoiniferter compound, a diiniferter compound, and a tetrainiferter compound, respectively, which are useful in preparing photoiniferter block polymers which are useful in the dental composition of the present invention.

EXAMPLE 1

Synthesis of Monofunctional Photoiniferter Benzyl Carbazolyldithiocarbamate (CDC)

Into a 250 ml volume flask fitted with a magnetic stirrer and a Dean-Stark trap were charged 35.85 parts of carbazole, 12 parts of potassium hydroxide, and 132 parts of xylene. The mixture was refluxed to remove water. A light yellow-colored solid, the potassium salt of carbazole, was removed by suction filtration. An excess of carbon disulfide was added to 21.7 parts of potassium carbazole dissolved in 100 parts of dimethyl formamide. A mildly exothermic reaction occurred and the resultant solution was stirred overnight at room temperature. A dark maroon colored solution was obtained. The addition of 13.3 parts of benzyl chloride changed the color of the solution to that of a lighter maroon. After stirring the solution for about 5 hours, the reaction was quenched with water. Next, 100 parts of methylene chloride was added and the reaction mixture was washed three times with water. The organic layer was dried over anhydrous magnesium sulfate and filtered. Upon concentration of the filtrate under vacuum, a bright yellow-colored solid was obtained. The solid was recrystallized from diethyl ether:hexanes. Nuclear magnetic resonance spectroscopy confirmed the presence of pure benzyl carbazolyldithiocarbamate, m.p. 66°–68° C.

EXAMPLE 2

Synthesis of Difunctional Photoiniferter Xylylene bis(N,N-diethyldithiocarbamate) (XDC)

Into a 1-liter three-necked flask fitted with a mechanical stirrer were charged 89.7 parts of 2,2'-dichloro-p-xylene and 764 parts of ethanol. Next, 235 parts diethyl dithiocarbamic acid sodium salt $(C_2H_5)_2NCS_2Na \cdot 3H_2O$ were charged into the flask. The mixture was stirred at room temperature for about three hours. A heavy solid precipitate of sodium chloride was observed. Next, 444 parts of chloroform were added to the reaction mixture and the solution was stirred overnight. The reaction mixture was then filtered to remove the sodium chloride precipitate. The filtrate was placed in a 1,000 ml volume flask and the solvent removed by rotary evaporation. The solid obtained was dissolved in chloroform and washed four times with water. The chloroform layer was dried over anhydrous magnesium sulfate and filtered following which the solvent was removed by rotary evaporation. The white solid obtained was recrystallized from ethanol. Nuclear magnetic resonance spectroscopy confirmed the presence of pure XDC compound, m.p. 78°–80° C.

EXAMPLE 3

Synthesis of Tetrafunctional Photoiniferter—durene $\alpha,\alpha',\alpha'',\alpha'''$-tetrakis-dithiocarbamate (DDC)

Into a 500 ml round-bottom flask was charged 25 parts of durene, 133 parts of N-bromosuccinimide, 175 parts of carbon tetrachloride and 0.83 parts benzoyl peroxide. The mixture was refluxed for about four hours and subsequently filtered. The filtrate was concentrated by rotary evaporation and the residual solid was recrystallized from diethyl ether. Nuclear magnetic resonance spectroscopic analysis of the solid confirmed the presence of $\alpha,\alpha',\alpha'',\alpha'''$-tetrabromodurene (TBD). To 2.36 parts of TBD and 26 parts of tetrahydrofuran contained in a 100 ml flask were added 4.8 parts of sodium diethyldithiocarbamate dissolved in 17 parts of tetrahydrofuran. Sodium bromide precipitated out immediately as a white solid. After stirring for about four hours at room temperature, the reaction mixture was filtered to remove the sodium bromide precipitate. The filtrate was concentrated by rotary evaporation and the residual waxy solid was recrystallized from ethanol to yield a white crystalline solid. Nuclear magnetic resonance spectroscopic analysis confirmed the structure to be durene $\alpha,\alpha',\alpha'',\alpha'''$-tetrakis-dithiocarbamate.

EXAMPLES 4–6

Examples 4, 5 and 6 describe the preparation of photoiniferter block polymers of the formula $I(BT)_n$ utilizing the difunctional photoiniferter compound of Example 2, the monofunctional photoiniferter compound of Example 1, and the tetrafunctional photoiniferter compound of Example 3, respectively.

EXAMPLE 4

Synthesis of Xylene bis(N,N-diethyldithiocarbamate) (XDC)-poly MMA $[I(BT)_n]$ n=2

Into a 237 ml clear flint glass bottle were charged 30 parts of methyl methacrylate (MMA), 0.53 parts of xylene bis (N,N-diethyldithiocarbamate) [XDC] prepared according to the procedure of Example 2, and 30 parts of ethyl acetate. The solution was purged with nitrogen gas for about 10 minutes, following which the the bottle was sealed, placed on a roller mill, and irradiated with a bank of six General Electric (GE) 15 watt cylindrical black light lamps. The mixture became progressively more viscous. The completion of the reaction was monitored by nuclear magnetic resonance spectroscopy and gas chromatography until the presence of monomer could no longer be detected. Analysis by gel permeation chromotography (GPC) showed the XDC-poly MMA to have a number average molecular weight of 42,183 and a polydispersity of 1.82.

EXAMPLE 5

Synthesis of Carbazole-N-dithiocarbamate (CDC)-poly MMA $[I(BT)_n]$ n=1

Into a 237 ml clear flint glass bottle were charged 25 parts of methyl methacrylate, 1.0 part of monofunctional photoiniferter carbazolyldithiocarbamate (CDC) prepared according to the procedure of Example 1, and 30 parts of ethyl acetate. The solution was purged with nitrogen gas for about 10 minutes after which the the bottle was sealed and irradiated as described in Example 4. After completion of the polymerization, the reaction mixture was diluted with a large excess of methanol. A fine light yellow solid precipitate was obtained. The precipitate was isolated by filtration and dried. Molecular weight determination by GPC showed $\overline{M}_n=27,943$, $\overline{M}_w=47,161$ and polydispersity of $\rho=1.69$ with absorption at 250–450 nm.

EXAMPLE 6

Synthesis of durene $\alpha,\alpha',\alpha''',\alpha'''$-tetrakis dithiocarbamate (DDC)-poly MMA $[I(BT)_n]$, n=4

Into a 237 ml clear flint glass bottle were charged 10 parts of methyl methacrylate, 0.38 part of the tetrafunctional photoiniferter durene $\alpha,\alpha',\alpha''',\alpha'''$-tetrakis-dithiocarbamate (DDC) prepared according to the method of Example 3, and 15 parts of ethyl acetate. The solution was purged with nitrogen gas for 10 minutes and irradiated as described in Example 4. The resulting solution was diluted with 200 parts of methanol upon which the polymer precipitated. The polymer was subsequently isolated by filtration and dried in a vacuum oven at 50° C. GPC analysis showed the $\overline{M}_n=28,000$ and the polydispersity=2.0.

EXAMPLES 7–9

Examples 7–9 relate to the synthesis of triblock copolymers of the formula $I(BAT)_n$ formed utilizing the difunctional photoiniferter compound of Example 2. The triblock copolymers of Examples 7–9 are useful for inclusion in the dental composition of the present invention.

EXAMPLE 7

Synthesis of copoly(phenethyl methacrylate-butyl acrylate-phenethyl methacrylate) Triblock Copolymer [PEMA - BA- PEMA 10:80:10] [I(BAT)$_n$] n=2

Into a 355 ml clear glass flint bottle were charged 100 parts of butyl acrylate (BA), 1.5 parts of xylylenedithiocarbamate (XDC) prepared according to the method of Example 2, and 130 parts of ethyl acetate. The solution was purged with nitrogen gas and irradiated according to the method set forth in Example 4. The reaction mixture became progressively more viscous. The completion of the reaction was monitored by nuclear magnetic resonance spectroscopy until the vinyl peaks could no longer be detected. GPC analysis revealed the polybutyl acrylate-XDC to have a $\overline{M}_n$=42,400 and a polydispersity=2.7. Into a 237 ml clear flint glass bottle were charged 46 parts of the above isolated polyBA-XDC, [I(BT)$_n$], 5 parts of phenethyl methacrylate (PEMA), and 76.5 parts of ethyl acetate. After purging for 10 minutes with nitrogen gas and sealing the bottle, the mixture was irradiated for 40 hours in a roller mill with six General Electric (GE) 15 Watt fluorescent lamps. The polymer was then precipitated by the addition of 400 parts of methanol. The precipitated polymer was separated by filtration and dried in a vacuum oven at 50° C.

EXAMPLE 8

Synthesis of Copoly(isobornyl methacrylate-butyl acrylate-isobornylmethacrylate) Triblock Copolymer [iBoMA - BA -iBoMA 10:80:10] [I(BAT)$_n$] n=2

Into a 355 ml clear flint glass bottle were charged 46 parts of polybutyl acrylate-XDC, [I(BT)$_n$], prepared according to the method of Example 7, 5 parts of isobornyl methacrylate, and 76.5 parts of ethyl acetate. The solution was purged and irradiated and the polymer isolated and dried as described in Example 7.

EXAMPLE 9

Synthesis of Copoly(methyl methacrylate-butyl acrylate-methyl methacrylate 25:50:25) Triblock Copolymer [I(BAT)$_n$] n=2

Into a 355 ml clear flint glass bottle were placed 113 parts of butyl acrylate, 1.5 parts of difunctional photoiniferter xylylene bis(N,N-diethyldithio carbamate) (XDC), prepared according to the method of Example 2, and 113 parts of toluene. The solution was purged with nitrogen gas for 10 minutes and irradiated according to the procedure set forth in Example 4 for 24 hours. Into a 237 ml clear flint glass bottle were charged 53.1 parts of the polybutyl acrylate-XDC obtained above, 40 parts of methyl methacrylate, and 43.7 parts of toluene. The resultant solution was purged and irradiated according to the procedure set forth in Example 4 for 19 hours. The polymer was precipitated by the addition of 400 parts of methanol, separated by filtration, and dried in a vacuum oven at 50° C. Nuclear magnetic resonance spectroscopic analysis revealed the butyl acrylate to methyl methacrylate mole ratio to be 50:50.

EXAMPLES 10-14

Examples 10-14 relate to dental composition experiments which for simplicity reasons did not include a filler.

COMPARATIVE EXAMPLE 10

Involving the Polymerization of TEGDMA in the Presence and Absence of XDC-PMMA

A 5 gram portion of the solution of photoiniferter block polymer XDC-PMMA [I(BT)$_n$] of Example 4 was precipitated in 25 ml of diethyl ether by rapid stirring. The precipitated white polymer was filtered, washed with diethyl ether, and dried in vacuuo. The precipitated photoiniferter block polymer XDC-PMMA was then dissolved in 5.7 parts of triethyleneglycol dimethacrylate (TEGDMA) C(D)$_x$ monomer in a glass bottle in order to form a dental composition. No initiators or sensitizers were included in the dental composition. The resultant dental composition was irradiated in a Kulzer curing chamber (available from Kulzer Dental Company) fitted with a pulsed xenon lamp having a minimum wattage of 45 watts and a maximum wattage of 1300 watts. After 90 seconds of irradiation, a gelled material was observed. This gelled material was subjected to a second 90 second exposure, resulting in the formation of a hard set material.

A control experiment was performed which involved the irradiation of TEGDMA alone. 5.7 parts of TEGDMA was placed in a bottle which was irradiated in the Kulzer curing chamber for 90 seconds. No gelation was observed after the first 90 second exposure and following the second 90 second exposure only a trace of gellation was observed. Comparative Example 10 thus demonstrates that photoiniferter block polymer XDC-PMMA can induce the polymerization of C(D)$_x$ monomer upon exposure to ultraviolet radiation.

EXAMPLE 11

Curing of XDC-poly MMA in Combination with Various C(D)$_x$ Monomers

The precipitated XDC-Poly MMA [I(BT)$_n$] prepared acording to the method of Example 10 was dissolved in a number of different C(D)$_x$ monomers as shown in Table I below, in order to form viscous dental composition Samples 11a-e.

TABLE I

| Sample | C(D)$_x$ Monomer | Parts of Monomer | Parts of XDC-PMMA |
|---|---|---|---|
| 11a | TEGDMA | 1 | 1.77 |
| 11b | Butyl acrylate | 1 | 2.5 |
| 11c | Butyl acrylate | 4 | 1.0 |
| 11d | Phenethyl methacrylate | 1 | 2.5 |
| 11e | Norbornyl acrylate | 4 | 1.0 |

Each of the above Samples 11a-e were transferred to the pulsed xenon lamp curing unit described in Example 10. 3.888 grams of each sample was placed in a separate open glass vial. The xenon lamp curing unit was flushed with nitrogen gas for one minute and then subjected to a nitrogen pressure of 1.16×10$^2$ Pascals. Sequential 90 second exposures were used to irradiate each sample. A filter was used to eliminate radiation below 280 nm and above 850 nm. The nature of each irradiated sample after each exposure was rated in terms of consistency. The ratings for Samples 11a-e are provided in the Remarks Section of Table II below.

TABLE II

| Sample | Number of 90 Second Exposures | Remarks |
|---|---|---|
| 11a | 1 | Soft putty |

TABLE II-continued

| Sample | Number of 90 Second Exposures | Remarks |
|---|---|---|
|  | 2 | Hard putty, carvable |
|  | 3 | Hard, glassy, Barcol 46/46 |
| 11b | 1 | Hard material |
| 11c | 1 | Butylacrylate lost by evaporation |
| 11d | 1 | Viscosity increased |
|  | 2 | Soft putty |
|  | 3 | Hard putty |
|  | 4 | Carvable |
|  | 5 | Hard, glassy, Barcol 35/30 |
| 11e | 1 | Heavy consistency |
|  | 2 |  |
|  | 3 | Soft putty |
|  | 4 | Carvable |
|  | 5 | Hard, but still carvable |
|  | 6 | Glassy |

Example 11 demonstrates that the physical nature of the dental composition can be controlled by controlling the exposure of the dental composition to the radiation source. Thus, after 2 exposures the dental composition Sample 11d cured to a soft putty, after 3 exposures it obtained a consistency such that it was harder and shapeable, after 4 exposures it was carvable, and after 5 exposures its shape was fixed.

The purpose of Examples 12, 13 and 14 was to demonstrate whether the radiant energy source curing of a dental composition could take place in the absence of a photoiniferter block polymer.

EXAMPLES 12 AND 13 AND COMPARATIVE EXAMPLE 14

The solutions used for Examples 12-14 are set forth in Table III below. Approximtely 0.4 ml portions of each of the solutions were placed in separate 0.38 cm Teflon TM molds, each mold having a 7 mm diameter and a 2.5 mm deep cylindrical hole through the center thereof. Polyester sheets each having a thickness of 0.05 mm were placed on the top and bottom surfaces of the mold to exclude air and squeeze out excess solution. The solutions contained in each mold were then separately irradiated for specified time periods with a Visilux TM 2 dental curing light (available from 3M). A Barcol hardness evaluation of the top (exposed) and bottom surfaces of the samples was performed using an indenter available commercially from the Barber Colman Company, yielding hardness values of the "B" scale.

TABLE III

| Example | Solution Composition (parts) |  | Irradiation Time (sec.) | Properties | Barcol Hardness Top/Bottom |
|---|---|---|---|---|---|
| 12 | CDC-poly MMA | 1 | 40 | Firm, carvable | * |
|  | TEGDMA | 1.5 | 40 | Harder | 10/8 |
|  | BIS-GMA | 1.5 | 40 | Glassy | 35/32 |
|  | Camphorquinone | 0.02 |  |  |  |
| 13 | DDC-poly MMA | 1 | 10 | Hard | 20/8 |
|  | TEGDMA | 1.5 | 10 | Glassy | 40/38 |
|  | BIS-GMA | 1.5 |  |  |  |
|  | Camphorquinone | 0.02 |  |  |  |
| 14 | TEGDMA | 1.5 | 120 | No cure | * |
|  | BIS-GMA | 1.5 |  |  |  |
|  | Camphorquinone | 0.02 |  |  |  |

*No reading with the Barcol hardness tester was obtainable.

The data contained in Table III demonstrates that a photoiniferter system is essential for the curing reaction to occur since the composition of Example 14 which did not contain a photoiniferter did not cure.

EXAMPLE 15

Preparation and Curing of a Dental Composition Useful as a Restorative

The following ingredients were charged into a glass vial:

| | |
|---|---|
| Copoly(IBoMA-BA-IBoMA) (of Example 8) | 6.48 parts |
| Isobornyl methacrylate | 6.48 parts |
| Triethyleneglycol dimethacrylate | 3.00 parts |
| BIS-GMA | 3.00 parts |
| Camphorquinone | 0.092 parts |

The glass vial was then sealed and placed on a roll mill for about 4 hours in order to form a homogeneous solution. To 14.82 parts of the resulting homogeneous solution were added 4.81 parts of diatomaceous silica and 1.40 parts of precipitated silica in order to form a mixture. The mixture was spatulated in order to provide a smooth paste. A portion of the paste was placed in a 3.8 cm×0.762 cm×0.127 cm rectangular plexiglass mold which was then placed in a specially designed curing unit. The specially designed curing unit was equipped with a high intensity 650 watt tungsten halogen light source which emitted radiation. In addition, the curing unit was equipped with optional pressure and vacuum curing cycles. The curing unit utilized an external vacuum pump and in addition was attached to a pressurized air source of $2.75$–$4.0 \times 10^5$ Pascals. The light source exposure settings were capable of being varied. The actual time of illumination of the curing unit chamber corresponding to the switch settings (1–10) are set forth below.

| Time of Illumination of Curing Unit Chamber | |
|---|---|
| Switch Setting | Time (Min:secs.) |
| 1 | 0:25 |
| 2 | 0:32 |
| 3 | 0:42 |
| 4 | 0:55 |
| 5 | 1:11 |
| 6 | 1:33 |
| 7 | 2:01 |
| 8 | 2:37 |
| 9 | 3:24 |
| 10 | 4:25 |

The sample composition was subjected to exposures of "light only" in the curing unit chamber at setting 3 (42 second exposure). The properties of the sample composition were measured initially by indentation with a 300 gram Gilmore needle and are described in Table IV.

The sample was allowed to stand at ambient conditions for 1 minute between exposures.

TABLE IV

| Number of Exposures | Total Exposure Time (min:sec.) | Properties |
| --- | --- | --- |
| 1 | 0:42 | Soft, flowable |
| 2 | 1:24 | Putty-like |
| 3 | 2:06 | Firm, indentable |
| 4 | 2:48 | Firm, elastic |
| 5 | 3:30 | Hard, not indentable |

After 3 exposures the sample composition could be shaped at which point it was at a consistency which would be useful in forming a denture base or a restorative. After 4 exposures it could be carved at which point it would be useful for final fitting as a denture base. After exposure 5, the final shape was fixed. The data contained in Table IV demonstrates controlled curing of a restorative dental composition.

EXAMPLE 16

Preparation of a Dental Composition Useful as a Denture Liner

Into a glass vial were charged the following:

| | |
| --- | --- |
| Copoly(phenethyl methacrylate-butyl acrylate-phenethyl methacrylate) [10:80:10] (of Example 7) | 7.74 parts |
| Isobornyl methacrylate | 7.74 parts |
| BIS-GMA | 3.00 parts |
| Triethyleneglycol dimethacrylate | 3.00 parts |
| Camphorquinone | 0.108 part |

The contents of the glass bottle were mixed by sealing the glass bottle and roll milling the bottle for about 4 hours in order to yield a homogeneous solution. To 14.82 parts of the resulting homogeneous solution were added 4.79 parts of diatomaceous silica and 1.41 parts of precipitated silica. The mixture was spatulated to provide a smooth paste. A portion of the paste was cured as described in Example 15. The results are set forth in Table V.

TABLE V

| Number of Exposures | Total Exposure Time (min.:sec.) | Properties |
| --- | --- | --- |
| 1 | 0:42 | Soft |
| 2 | 1:24 | Putty-like, carvable |
| 3 | 2:06 | Firm, slight indentation |
| 4 | 2:48 | Firm, no indentation |
| 5 | 3:30 | Firm, no indentation |

The tensile strength, percent elongation and modulus of the sample prepared according to Example 16 are reported in Table VII below.

EXAMPLE 17

Preparation of a Dental Composition Useful as a Denture Base

Into a glass vial were charged the following:

| | |
| --- | --- |
| Copoly(methyl methacrylate-butyl acrylate-methyl methacrylate) [25:50:25] (of Example 9) | 8.0 parts |
| Isobornyl methacrylate | 5.0 parts |
| BIS-GMA | 3.5 parts |
| Triethyleneglycol dimethacrylate | 3.5 parts |
| Camphorquinone | 0.1 parts |

The glass vial was then sealed and placed on a roll mill for about 6 hours in order to form a homogeneous solution. To the resulting homogeneous solution was added 1.3 parts of Cab-O-Sil fumed silica (available from Cabot Corporation) in order to form a mixture. The mixture was spatulated in order to provide a smooth paste. A portion of the dental composition paste was cured as described in Example 15.

Table VI below sets forth the properties of the dental composition paste of Example 17 after exposure in the curing unit chamber.

TABLE VI

| Number of Exposures | Total Exposure Time (min.:sec.) | Properties |
| --- | --- | --- |
| 1 | 0:42 | Soft |
| 2 | 1:24 | Firm, putty-like, carvable |
| 3 | 2:06 | Hard |
| 4 | 2:48 | Hard, glassy |

The data contained in Table VI demonstrates the effect of controlled curing on the properties of the dental composition. The tensile strength, percent elongation and modulus of the dental composition sample prepared according to Example 17 are reported in Table VII below.

Measurement of Tensile Properties

The tensile properties of the dental compositions prepared according to Examples 15–17 were measured after the fourth and fifth successive exposures. The sample preparation was as follows. Portions of the dental composition pastes prepared according to Examples 15–17 were packed into three separate rectangular plexiglass molds, each mold having a length of 3.81 centimeters, a width of 0.762 centimeter, and a thickness of 0.127 centimeter. The top of each mold was then covered with a plexiglass plate and a 300 gram weight was placed on each plexiglass plate in order to remove air bubbles from the paste samples. The weights were then removed and each paste sample was separately placed in the curing unit and exposed at the desired cycle for the appropriate time periods. After the exposures were completed the samples were allowed to stand for approximately 1 hour at 37° C. and 95% relative humidity, and subsequently removed from the molds. In some instances a silicone die-release material was used on the inside of the molds in order to facilitate removal of the cured paste sample. Two marks were placed on each cured paste sample at a distance of 2.54 centimeters apart. The cured paste samples were then placed in distilled water and aged at 37° C. for 24 hours. The cure paste samples were then clamped in an Instron ™ testing machine so that the jaws of the Instron testing machine were aligned along the two marks. This ensured that the distance of separation of the jaws was always 2.54 cm. The properties of the cured paste samples were then tested in tension. The following formulae were used for calculating the numerical values of the properties measured.

$$\text{Tensile} = \frac{\text{Force at Break}}{\text{Width} \times \text{Thickness}}$$

$$\text{Modulus} = \frac{\text{Force} \times \text{Initial Length}}{\text{Width} \times \text{Thickness} \times \text{Final Length}}$$

$$\frac{\text{\% Elongation}}{\text{at break}} = \frac{\text{Final Length} - \text{Original Length}}{\text{Original Length}} \times 100$$

The elongation, tensile strength and modulus of the paste samples prepared according to Examples 15-17 which had been cured after four and five exposures at setting 3 are set forth in Table VII. Measurements could not be taken after exposures one, two, and three since sufficient polymerization and crosslinking had not yet occurred.

An examination of the values obtained reveals that further curing occurred with additional exposure as evidenced by the increase in tensile strength and modulus and the decrease in elongation as the exposure continued. The paste samples after the fourth and fifth exposures exhibited properties which would make them suitable for use as denture liners.

TABLE VII

Tensile Properties of the Cured Dental Composition Samples of Examples 15-17

| Ex. | Number of Exposures | Total Exposure Time (min:sec) | Elongation (%) | Tensile Strength (MPa) | Modulus (MPa) |
|---|---|---|---|---|---|
| 15 | 4 | 2:48 | 72 | 2.075 | 0.421 |
| 15 | 5 | 3:30 | 59 | 3.192 | 0.656 |
| 16 | 4 | 2:48 | 65 | 2.213 | 0.408 |
| 16 | 5 | 3:30 | 48 | 3.364 | 0.586 |
| 17 | 3 | 2:06 | 27 | 10.775 | 641.142 |
| 17 | 4 | 2:48 | 6 | 43.439 | 1371.906 |

EXAMPLE 18

Preparation of a Dental Composition Useful as a Dental Restorative

Into a glass bottle were charged the following:

| | |
|---|---|
| Copoly(methyl methacrylate-butyl acrylate-methyl methacrylate) [25:50:25] (from Example 9) | 37.5 parts |
| Methyl methacrylate | 22.5 parts |
| BIS-GMA | 19.8 parts |
| Triethyleneglycol dimethacrylate | 19.8 parts |
| Camphorquinone | 0.3 parts |

The glass bottle was then sealed and placed in a mechanical shaker for about 18 hours in order to provide a homogeneous solution. To 67 parts of the homogeneous solution were added 113 parts of a mixture of zirconia:-silica filler (5.5:1 mole ratio of $SiO_2$:$ZrO_2$ filler prepared for filtered sols according to the method described in U.S. Pat. No. 4,503,169, incorporated by reference herein, and containing 20% "OX-50" TM submicron filler) which had previously been treated with gamma-methacryoxy-propyltrimethoxy silane. A smooth dental composition paste was prepared by spatulation. A portion of the dental composition paste was placed in two separate 0.38 cm³ Teflon TM polytetrafluoroethylene molds, each mold having a 7 mm diameter and a 2.5 mm deep cylindrical hole through the center thereof. Polyester sheets (2 mil thick) were placed on the top and bottom of each mold to exclude air and squeeze out excess paste. The paste samples were then irradiated with a Visilus TM 2 dental curing light for various periods of time. The two paste samples were sequentially cured. After 5 seconds of exposure, each paste sample was of the consistency of a soft, packable putty. After 10 addditional seconds (15 seconds total) each paste sample was carvable, but still indentable by a 300 gram Gilmore needle. After an additional 10 seconds of exposure (25 seconds total), hard cured paste samples were obtained. Measurement of the Barcol hardness for both cured paste samples yielded a mean average value of 75 for the top sides for both paste samples and a mean average value of 68 for the bottom sides of both samples.

For diametral tensile strength measurements, uncured paste was packed into five separate glass tubes, each tube having a 4 mm inner diameter. Each paste sample was then subjected to $2.75 \times 10^5$ Pascals pressure for 5 minutes and cured by exposure to a Visilux TM 2 curing light. The cured pastes from each sample were cut on a diamond saw to form 2 mm long cylindrical plugs. The plugs were stored in distilled water at 37° C. for 24 hours after which their diametral tensile strengths were determined according to ADA (American Dental Association) specification No. 27 using an Instron tensile tester. The compressive strength was determined for five samples similarly prepared, although each sample was cut to a length of 8 mm according to ADA specification No. 9. The diametral tensile and compressive strength mean average values for the cured paste samples are provided in Table VIII.

EXAMPLE 19

Preparation of a Dental Composition Useful as a Dental Restorative

Into a clear glass flint bottle were charged the following:

| | |
|---|---|
| XDC-PMMA (prepared according to Example 4) | 37.1 parts |
| Norbornyl acrylate | 41.9 parts |
| Triethyleneglycol dimethacrylate | 21.0 parts |
| Camphorquinone | 0.5 parts |

The contents of the glass bottle were mixed by sealing the bottle and roll milling the sealed bottle to yield a homogeneous solution. Two parts of the homogeneous solution and 13.3 parts of the filler mixture used in Example 18 were combined and spatulated in order to provide a smooth paste. Curing of a portion of the paste in a 0.38 cm³ Teflon TM polytetrafluoroethylene mold having a circular hole 2.5 mm deep and a 7 mm diameter using a Visilux TM 2 dental curing light available from 3M Company yielded a hard mass in 10 seconds. Results of the curing of the paste sample are reported in Table VIII, Example 19.

Another portion of the paste was then cured in an identical mold at Setting 1 in the curing unit described in Example 15. Results of curing of the paste sample of Example 19 in the curing unit of Example 15 are reported in Table IX.

TABLE VIII

| Example | Compressive Strength (MPa) | Diametral Tensile Strength (MPa) | Barcol Hardness Top/Bottom |
|---|---|---|---|
| 18 | 403 | 71.7 | 75/68 |
| 19 | 422 | 83.4 | 85/85 |

TABLE IX

| Number of Exposures | Total Exposure Time (Minutes:seconds.) | Properties | Barcol Hardness Top/Bottom |
| --- | --- | --- | --- |
| 1 | 0:25 | Soft, carvable | |
| 2 | 0:50 | Firm, carvable | |
| 3 | 1:15 | Hard | 70/65 |
| 4 | 2:40 | Hard | 85/85 |

The physical property measurements of the dental composition after final cure are described in Table VIII.

EXAMPLE 20

Preparation of a Dental Composition Useful as a Dental Restorative

Into a clear glass flint bottle were charged the following:

| | |
| --- | --- |
| DDC-MMA (prepared according to Example 6) | 37.0 parts |
| Norbornyl methacrylate | 42.0 parts |
| TEGDMA | 21.0 parts |
| Champhorquinone | 0.5 parts |

The contents of the glass bottle were mixed by sealing the glass bottle and roll milling the bottle in order to yield a homogeneous solution. To 2 parts of the resulting solution were added 13.3 parts of the filler mixture of Example 18 after which the resultant mixture was spatulated in order to provide a smooth paste. A portion of the paste was placed in a 0.38 $cm^3$ volume Teflon TM mold having a 7 mm diameter and a 2.5 mm deep cylindrical hole through the center thereof. The paste was then cured in the curing unit as described in Example 15. The Barcol Hardness results are provided in Table X below.

TABLE X

| Number of Exposures | Total Exposure Time (Minutes:seconds) | Properties | Barcol Hardness Top/Bottom |
| --- | --- | --- | --- |
| 1 | 0:25 | Firm putty | |
| 2 | 0:50 | Hard | 45/42 |
| 3 | 1:15 | Hard | 85/85 |

EXAMPLES 21-22

Examples 21 and 22 relate to experiments involving the effect of a metal compound accelerator on the polymerization of dental compositions which did not contain a filler for simplicity reasons.

EXAMPLE 21

Control Experiment Involving the Preparation of a Dental Composition in the Absence of Sn(Oct)$_2$ Metal Compound Accelerator Into a 237 ml glass bottle were charged the following:

| | |
| --- | --- |
| Block copoly(methyl methacrylate-methacrylate) [25:50:25] (from Example 9) | 37.5 parts |
| Methyl methacrylate | 22.5 parts |
| BIS-GMA | 19.8 parts |
| Triethyleneglycol dimethacrylate | 19.8 parts |

The contents of the glass bottle were mixed by sealing the glass bottle and roll milling the bottle for several hours in order to yield a homogeneous solution. Next, 13.8 parts of the homogeneous solution was placed in a circular pan having a diameter of 6.6 mm and a depth of 1.6 mm which was then placed in the photocell chamber of a Differential Photocalorimeter (Model #930, E. I. du Pont De Nemours & Co.). The cell was maintained under a nitrogen atmosphere and the sample was irradiated with a 200 Watt mercury lamp for 2 minutes. The enthalpy was measured since enthalpy is directly proportional to the rate of polymerization. The observed enthalpy was 29.1 J/g.

EXAMPLE 22

Preparation of a Dental Composition in the Presence of Sn(Oct)$_2$ Metal Component Accelerator Into a 237 ml glass bottle were charged the following:

| | |
| --- | --- |
| Block copoly(methyl methacrylate-butyl acrylate-methyl methacrylate) [25:50:25] (from Example 9) | 37.5 parts |
| Methyl methacrylate | 22.5 parts |
| BIS-GMA | 19.8 parts |
| Triethyleneglycol dimethacrylate | 19.8 parts |
| Stannous 2-ethyl hexanoate (Accelerator Compound) | 12.3 parts |

The contents of the glass bottle were mixed by sealing the glass bottle and roll milling the bottle for several hours in order to yield a homogeneous solution. Next, 14.5 parts of the homogeneous solution were placed in a circular pan having a diameter of 6.6 mm and a depth of 1.6 mm. The pan containing the solution was then placed in the photocell chamber of a Differential Photocalorimeter as described in Example 21. The cell was maintained under a nitrogen atmosphere and the sample was irradiated with a high pressure mercury lamp for 2 minutes. The observed enthalpy was 79.7 J/g indicating a higher reaction rate when a metal compound accelerator compound is used. The use of a metal compound accelerator resulted in a 2.7 times faster reaction rate.

While this invention has been described in connection with specific embodiments, it should be understood that it is capable of further modification. The claims herein are intended to cover those variations which one skilled in the art would recognize as the chemical equivalent of what has been described here.

We claim:

1. A stageably curable dental composition, comprising:
   a mixture of
   (i) acrylic photoiniferter block polymer selected from the group consisting of I(BT)$_n$, I(BAT)$_n$, and mixtures thereof, wherein
   I represents the free radical initiator portion of an iniferter of the formula I(T)$_n$;
   T represents the terminator portion of said iniferter;
   n is an integer of at least 1;
   wherein I(T)$_n$ is capable upon being subjected to a radiant energy source of forming free radical I($\cdot$)$_n$ nT$\cdot$, I$\cdot$ is a highly reactive free radical capable of initiating free radical polymerization, and T$\cdot$ is a less reactive free radical which is generally much less capable of initiating free radical polymerization than I$\cdot$ but will rejoin with I(19 )$_n$ or a free radical polymer segment free radically polymerized with I(·)$_n$ upon termination of said radiant energy source;

B represents an acrylic polymer block having a glass transition temperature of about "200° C." to about 400° C.; and A represents a normally thermoplastic polymer block having a glass transition temperature of at least about 30° C.; and further wherein the glass transition temperature of block A is at least about 50° C. higher than that of block B;

(ii) a monomer charge comprising free radically polymerizable monomer of the formula C(D)$_x$ wherein x is an integer ranging from 1 to about 9;

D is an acrylate or methacrylate moiety; and

C is an alkyl, aryl, or aralkyl organic residue; and (iii) about 5 to about 90 weight % of a filler based upon the weight of said mixture;

wherein the weight ratio of photoiniferter block polymer to free radically polymerizable monomer of the formula C(D)$_x$ ranges from about 1:99 to about 99:1.

2. The dental composition of claim 1 wherein said acrylic photoiniferter block polymer has the formula I(BT)$_n$ and polymer block B has a glass transition temperature ranging from about −200° C. to about 400° C.

3. The dental composition of claim 1 wherein said photoiniferter block polymer has the formula I(BAT)$_n$ and wherein polymer block B has a glass transition temperature ranging from about −200° C. to about 100° C., polymer block A has a glass transition temperature ranging from about 30° C. to about 150° C., and the glass transition temperature of polymer block A is about 50° C. higher than the glass transition temperature of polymer block B.

4. The dental composition of claim 1 wherein said acrylic photoiniferter block polymer has the formula I(BAT)$_n$ and wherein the weight ratio of said polymer block B to said polymer block A ranges from about 95:5 to about 5:95.

5. The dental composition of claim 1 wherein said acrylic photoiniferter block polymer has the formula I(BT)$_n$ and wherein n is an integer ranging from 1 to about 12.

6. The dental composition of claim 5 wherein n is an integer ranging from 1 to about 6.

7. The dental composition of claim 1 wherein said acrylic photoiniferter block polymer has the formula I(BAT)$_n$ and wherein n is an integer ranging from 2 to about 12.

8. The dental composition of claim 6 wherein n is an integer ranging from about 2 to about 6.

9. The dental composition of claim 1 wherein said polymer block A is formed from monomer selected from the group consisting of methyl methacrylate, phenethyl methacrylate, isobornyl methacrylate, isopropyl methacrylate, n-propyl methacrylate, and mixtures thereof.

10. The dental composition of claim 1 wherein said acrylic photoiniferter block polymer has the formula I(BAT)$_n$ and wherein I(BAT)$_n$ is represented by the formula

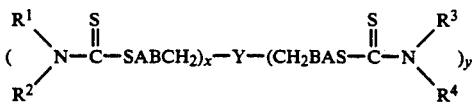

wherein

R$^1$, R$^2$, R$^3$ and R$^4$ are aliphatic or aromatic moieties which can be the same or different and which do not substantially interfere with the ability of I· to promote free radical polymerization or with the ability of T· to recombine with I· or a polymer free radical segment including I·;

Y is a linking group having a functionality of x+y which does not substantially interfere with the ability of I· to promote free radical polymerization or the ability of T· to recombine with I· or a polymer free radical segment including I·0; and x and y are each integers of at least 1 and the sum of x+y is not greater than about 12.

11. The dental composition of claim 1 wherein said iniferter is selected from the group consisting of benzyl carbazolylthiocarbamate, xylylene bis(N,N-diethyldithiocarbamate), durene α,α',α'',α'''-tetrakis(N,N-diethyldithiocarbamate), xylylene carbazolyldithiocarbamate, and mixtures thereof.

12. The dental composition of claim 1 wherein said polymer block B is formed of monomer selected from the group consisting of acrylic acid, methacrylic acid, esters of acrylic acid and alcohol, esters of methacrylic acid and alcohol, said alcohol comprising from 1 to about 22 carbon atoms, and mixtures thereof.

13. The dental composition of claim 1 wherein said free radically polymerizable monomer of the formula C(D)$_x$ is selected from the group consisting of alkyl, aryl, and aralkyl monoacrylates; alkyl, aryl, and aralkyl monomethacrylates; alkyl, aryl, and aralkyl diacrylates; alkyl, aryl, and aralkyl dimethacrylates; alkyl, aryl, and aralkyl multifunctional acrylates; alkyl, aryl, and aralkyl multifunctional methacrylates; and mixtures thereof, wherein said free radically polymerizable monomer optionally includes one or more non-interfering heteroatoms.

14. The dental composition of claim 1 wherein said free radically polymerizable monomer of the formula C(D)$_x$ is selected from the group consisting of butyl acrylate, phenethyl methacrylate, norbornyl acrylate, isobornyl methacrylate, diglycidyl methacrylate, ethoxylated bisphenol A dimethacrylate, diethylene glycol diacrylate, diethylene glycol methacrylate, triethylene glycol diacrylate, triethylene glycol dimethacrylate, 2,2-dimethylpropane diol diacrylate, 2,2-dimethylpropane diol dimethylacrylate, tetraethylene glycol diacrylate, tetraethylene glycol dimethacrylate, hexane diol diacrylate, hexane diol dimethacrylate, ethoxylated bisphenol A diacrylate, ethoxylated bisphenol A dimethacrylate, pentaerythritol trimethacrylate, pentaerythritol tetramethacrylate, and mixtures thereof.

15. The dental composition of claim 1 wherein said weight ratio of said photoiniferter block polymer to said free radically polymerizable monomer of the formula C(D)$_x$ ranges from about 10:90 to about 90:10.

16. The dental composition of claim 1 wherein said weight ratio of said acrylic photoiniferter block polymer to said free radically polymerizable monomer of the formula C(D)$_x$ ranges from 25:75 to about 75:25.

17. The dental composition of claim 1 which further comprises an additive selected from the group consisting of colorants, stabilizers, photosensitizers, medicaments, and mixtures thereof.

18. The dental composition of claim 1 which further comprises a polymerization accelerating amount of a metal compound, wherein said metal compound does not interact with said free radically polymerizable monomer in order to form an insoluble compound in an amount which would substantially interfere with said polymerization or crosslinking.

19. The dental composition of claim 18 wherein the metal compound is represented by the general formula $M_xL_x$ wherein M is a cation having a valency of z of a metal which is selected from the group consisting of tin, zinc, cobalt, titanium, palladium, and lead;

x is an integer of at least 1;

L is an anion having a valency of z which is selected from the group consisting of $C_{1-20}$ alkyl, aryl, $$-OR, -O-\overset{\overset{O}{\|}}{C}-R, NO_3^-, SO_4^=, \text{ and } PO_4^{-3};$$

R is selected form the group consisting of $C_{1-20}$ alkyl and aryl; and z is an integer of at least 1.

20. The dental composition of claim 18 wherein the metal compound is selected from the group consisting of stannous 2-ethylhexanoate, zinc 2-ethylhexanoate, and mixtures thereof.

21. The dental composition of claim 18 wherein said polymerization accelerating amount is about 0.1 to about 10 mole percent of metal compound based upon the monomer charge comprising free radically polymerizable monomer of the formula $C(D)_x$.

22. The dental composition of claim 1 which is useful in forming a denture base.

23. The dental composition of claim 1 which is useful in forming a denture liner.

24. The dental composition of claim 1 which is useful in forming a restorative.

* * * * *

UNITED STATES PATENT AND TRADEMARK OFFICE
CERTIFICATE OF CORRECTION

PATENT NO. : 5,318,999
DATED : June 7, 1994
INVENTOR(S) : Sumita B. Mitra et al.

Page 1 of 2

It is certified that error appears in the above-indentified patent and that said Letters Patent is hereby corrected as shown below:

Col. 3, line 56, "organic" should read --Organic--.

Col. 6, line 22, "in" should read --is--.

Col. 10, line 17, "500°" should read --50°--.

Col. 11, line 61, "radical" should read --radicals--.

Col. 12, line 40, insert a space between "-CH$_3$" and "for".

Col. 13, line 56, "CACO$_3$" should read --CaCO$_3$--.

Col. 14, line 62, "M$_x$L$_x$" should read --M$_x$L$_z$--.

Col. 15, line 3, insert a space between "C$_{1-20}$" and "alkyl".

Col. 17, line 52, "a,a',a'',a'''-tetrabromodurene" should read --$\alpha,\alpha',\alpha'',\alpha'''$-tetrabromodurene--.

Col. 17, line 64, "a,a',a'',a'''-tetrakis-dithiocarbamate" should read --$\alpha,\alpha',\alpha'',\alpha'''$-tetrakis-dithiocarbamate--.

Col. 18, line 16, delete "the" after "which".

Col. 18, line 35, delete "the" second occurrence before "bottle".

Col. 18, line 46, "a,a',a''',a''-tetrakis" should read --$\alpha,\alpha',\alpha'',\alpha'''$-tetrakis--.

Col. 18, line 51, "a,a',a''',a''-tetrakis-dithi-" should read --$\alpha,\alpha',\alpha'',\alpha'''$-tetrakis-dithi- --.

Col. 20, line 57, "10$^2$" should read --10$^{-2}$--.

Col. 25, line 53, "SiO$_2$.ZrO$_2$" should read -- SiO$_2$:ZrO$_2$--.

UNITED STATES PATENT AND TRADEMARK OFFICE
CERTIFICATE OF CORRECTION

PATENT NO. : 5,318,999
DATED : June 7, 1994
INVENTOR(S) : Sumita B. Mitra et al.

It is certified that error appears in the above-indentified patent and that said Letters Patent is hereby corrected as shown below:

Col. 27, line 23, "Champhorquinone" should read --Camphorquinone--.

Col. 28, line 62, "radical" should read --radicals-- and insert --and-- after "I(·)$_n$".

Col. 28, line 67, "I(19)$_n$" should read -- I(·)$_n$--.

Col. 29, line 4, "200°C" should read -- ~200°C--.

Col. 30, line 18, delete the "O" after "I·".

Col. 30, line 68, insert --about-- after "from".

Col. 31, line 16, "M$_x$L$_x$" should read --M$_x$L$_z$--.

Col. 32, line 6, "form" should read --from--.

Signed and Sealed this

Thirteenth Day of August, 1996

BRUCE LEHMAN

*Attest:*

*Attesting Officer*          Commissioner of Patents and Trademarks